(12) United States Patent
Hollister et al.

(10) Patent No.: US 9,724,226 B2
(45) Date of Patent: Aug. 8, 2017

(54) ORTHOPEDIC BRACE HAVING A SUPPORT MEMBER AND AN ADAPTED PAD

(75) Inventors: Matthew T. Hollister, Encinitas, CA (US); Christian L. Hansen, Vista, CA (US)

(73) Assignee: Breg, Inc., Carlsbad, CA (US)

( * ) Notice: Subject to any disclaimer, the term of this patent is extended or adjusted under 35 U.S.C. 154(b) by 1522 days.

(21) Appl. No.: 12/835,425

(22) Filed: Jul. 13, 2010

(65) Prior Publication Data

US 2012/0016283 A1    Jan. 19, 2012

(51) Int. Cl.
*A61F 5/00* (2006.01)
*A61F 5/01* (2006.01)

(52) U.S. Cl.
CPC .... *A61F 5/0123* (2013.01); *A61F 2005/0172* (2013.01); *Y10T 156/1052* (2015.01)

(58) Field of Classification Search
USPC ...... 602/14, 26, 23, 20, 5, 1, 17, 18, 13, 22, 602/21, 12, 16; 128/112.1, 113.1, 117.1, 128/889, 894, 846, 888; 36/3 R; 2/455, 2/44, 45, 414, 415, 20, 24, 267
See application file for complete search history.

(56) References Cited

U.S. PATENT DOCUMENTS

| | | | |
|---|---|---|---|
| 3,930,496 A | | 1/1976 | Gibbons |
| 5,450,625 A | * | 9/1995 | Hu ..................................... 2/16 |
| 6,021,780 A | | 2/2000 | Darby |
| 7,479,122 B2 | | 1/2009 | Ceriani et al. |
| 7,485,103 B2 | | 2/2009 | Mason et al. |
| 7,497,838 B1 | | 3/2009 | Dunagan |
| 7,658,720 B2 | | 2/2010 | Johnson, III |
| 7,704,218 B2 | | 4/2010 | Einarsson et al. |

* cited by examiner

*Primary Examiner* — Victoria J Hicks
(74) *Attorney, Agent, or Firm* — Rodney F. Brown

(57) ABSTRACT

An orthopedic brace is provided having a pliable pad and a rigid support member. The pad is fabricated from a laminate and has an integrally formed raised region and mesh section. The mesh section has a plurality of void spaces extending through the laminate which freely permit air flow therethrough. The support member has an open ventilation window extending through it which freely permits air flow therethrough. The support member overlays the pad with the ventilation window aligned with the underlying mesh section to freely permit air flow through the support member and pad via the aligned ventilation window and mesh section.

18 Claims, 5 Drawing Sheets

ORTHOPEDIC BRACE HAVING A SUPPORT MEMBER AND AN ADAPTED PAD

BACKGROUND OF THE INVENTION

The present invention relates generally to orthopedic braces, and more particularly to an orthopedic brace having a support member and a pad which is adapted to the configuration of the support member.

Orthopedic braces embody a broad range of structures, each having the common purpose of supporting and/or stabilizing a skeletal joint when worn on the body of a user. The orthopedic brace may serve either a preventative role or a remedial role. In a preventative role, the brace provides added support and stability to a healthy skeletal joint, thereby reducing the risk of injury when the joint is subjected to undue stress. In a remedial role, the brace supports and stabilizes a skeletal joint which has been weakened by injury or other infirmity, thereby reinforcing the joint and reducing the risk of further injury while the joint is rehabilitated.

Conventional orthopedic braces typically include a frame consisting of at least one support member positioned adjacent to the body of the person wearing the brace. In many cases, the frame has at least two support members which are positioned on either end of the skeletal joint being supported and/or stabilized. The support members may be dynamically interconnected by a hinge which is positioned at the skeletal joint to mimic the motion of the joint. For example, a conventional knee brace commonly includes a frame having an upper support member positioned adjacent to the upper leg of the wearer and a lower support member positioned adjacent to the lower leg of the wearer. A rotational hinge is positioned adjacent to the knee joint of the wearer which dynamically interconnects the upper and lower support members enabling controlled pivotal movement of the knee joint when the wearer engages in activity or rehabilitative therapy.

Orthopedic braces are typically secured to the body of the wearer by one or more straps which engage both the body and the frame of the brace. Orthopedic braces are also typically provided with padding which cushions the body of the wearer from the support members of the brace.

The present invention recognizes the importance and need for an orthopedic brace which precisely fits the wearer because a precise fit enhances both the functional performance of the brace and the comfort of the wearer. Accordingly, it is an object of the present invention to provide an orthopedic brace which comfortably and precisely fits the body of a wearer. In particular, it is an object of the present invention to provide an orthopedic brace which includes a support member and a pad positioned between the support member and the body when the brace is being worn which cushions the body from the support member. It is another object of the present invention to adapt the pad to the configuration of the support member which improves the fit of the brace on the body. It is another object of the present invention to provide the pad with flexion channels enabling the pad to readily conform to the contours of the body when the brace is being worn which optimizes the fit of the brace and maintains the brace in its desired position on the body. It is another object of the present invention to provide portions of the pad with a breathable mesh construction which ventilates the skin abutting the brace when the brace is being worn to minimize the build-up of perspiration between the skin and the brace. These objects and others are accomplished in accordance with the invention described hereafter.

SUMMARY OF THE INVENTION

One characterization of the present invention is an orthopedic brace comprising a pliable pad and a rigid support member. The pad is fabricated from a laminate and has a first face and a second face. The pad also has a raised region and a mesh section. The mesh section is preferably substantially thinner than the raised region. The mesh section is integrally formed in the laminate and has a plurality of void spaces extending through the laminate. The void spaces are preferably sufficiently large to freely permit air flow through the mesh section between the first face and the second face of the pad, but are sufficiently small to inhibit extrusion of skin on the body of a wearer through the mesh section between the first face and the second face of the pad.

The rigid support member has a first face, a second face and an open ventilation window extending through the support member which freely permits air flow between the first face and the second face of the support member. The support member overlays the pad with the ventilation window aligned with the underlying mesh section of the pad to freely permit air flow through the support member and pad via the aligned ventilation window and mesh section.

In accordance with one embodiment, the raised region is a first raised region. The pad also has a second raised region and a flexion channel between the first and second raised regions. The flexion channel is substantially thinner and more flexible than the first or second raised region enabling the pad to more freely flex along the flexion channel than across the first or second raised region.

In accordance with another embodiment, the laminate has a unitary construction comprising a first layer formed from a first material and a second layer formed from a second material. In another embodiment, the laminate further comprises a third layer and the second layer is positioned between the first layer and the third layer. In one embodiment, the third layer is formed from the first material. In another embodiment, the first material is a flexible fabric. In another embodiment, the second material is an elastically compressible foam.

In accordance with yet another embodiment, the orthopedic brace further comprises a strap connectable to the support member. The pad has a third raised region and a strap clearance segment substantially thinner than the first, second or third raised region. The strap clearance segment is positioned between the second and third raised regions and receives the strap when the strap is connected to the support member.

Another characterization of the present invention is a pad for an orthopedic brace comprising a pliable pad and a rigid support member. The pad has a posterior face and an anterior face. The pad is fabricated from a unitary laminate having an anterior external layer formed from a first flexible material, an internal layer formed from an elastically compressible material, and a posterior external layer formed from a second flexible material. The pad has a first raised region and a second raised region separated by a flexion channel which is substantially thinner than the first or second raised region enabling the pad to more freely flex along the flexion channel than across the first or second raised region. The pad also has a mesh section integrally formed in the laminate. The mesh section is substantially thinner than the first or second raised region and has a plurality of void spaces extending through the laminate which freely permit air flow through the mesh section between the posterior face and the anterior face of the pad.

The support member has an anterior face, a posterior face and an open ventilation window extending through the support member which freely permits air flow between the anterior face and the posterior face of the support member. The support member overlays the pad with the anterior face of the pad engaging the posterior face of the support member and the ventilation window aligned with the underlying mesh section of the pad to freely permit air flow through the support member and pad via the aligned ventilation window and mesh section.

Another characterization of the present invention is a method of forming a pad for an orthopedic brace. A first sheet of a first material, a second sheet of a second material, and a third sheet of a third material are stacked such that the second sheet is positioned between the first and third sheets. The first and third materials are flexible and the second material is elastically compressible. The second sheet is bonded to the first and third sheets to create a laminate having a first face, a second face and an essentially uniform thickness.

A blank is cut out from the first, second and third sheets which has the outline of a pad. An areal section of the blank is compressed beyond the elasticity limit of the second material such that the compressed areal section is permanently impressed into the blank and is substantially thinner than an adjoining raised region of the blank. Void spaces are cut out from the compressed areal section to define a mesh section. The void spaces extend entirely through the laminate freely permitting air flow through the mesh section between the first and second faces of the laminate.

In accordance with an alternate embodiment, the method further comprises compressing a narrow elongate segment in the raised region of the blank beyond the elasticity limit of the second material. A channel is permanently impressed into the blank dividing the raised region into a first raised region and a second raised region both substantially thicker than the channel. As a result, the channel is more flexible than the first or second raised region enabling the laminate to more freely flex along the channel than across the first or second raised region.

In accordance with another embodiment, the first material and the second material are both a fabric. In another embodiment, the first material and the second material are the same fabric. In another embodiment, the blank is cut out from the first, second and third sheets after the second sheet is bonded to the first and third sheets to create the laminate.

The present invention will be further understood from the drawings and the following detailed description.

Figure 1:
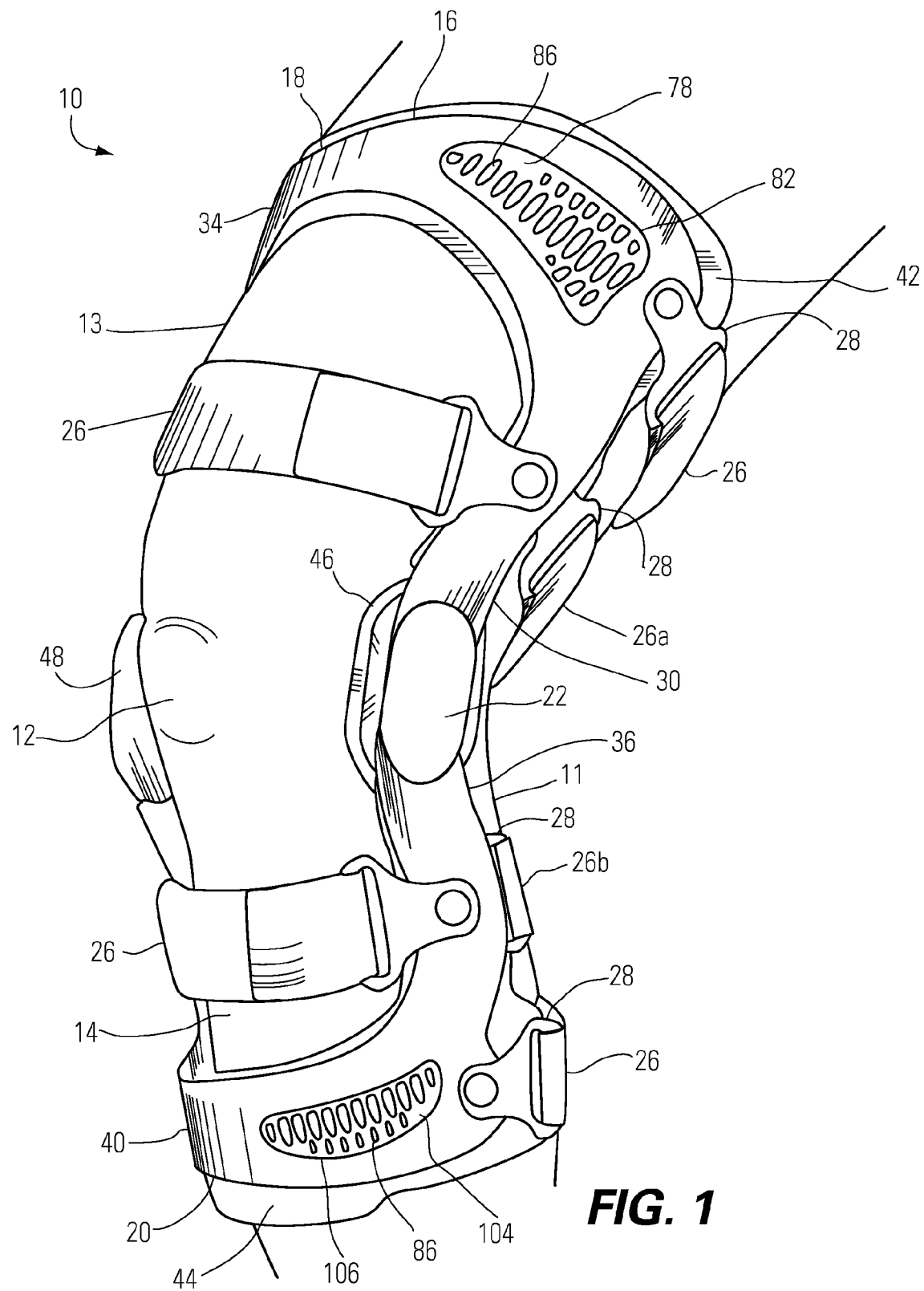
FIG. 1 is a perspective view of an orthopedic brace having a padded frame.

Embodiments of the invention are illustrated by way of example and not by way of limitation in the above-recited drawing figures, wherein like reference characters indicate the same or similar elements. It should be noted that common references herein to "an embodiment of the invention", "one embodiment of the invention", "an alternate embodiment of the invention", "a preferred embodiment of the invention", or similar such language are not necessarily references to the same embodiment of the present invention.

DESCRIPTION OF PREFERRED EMBODIMENTS

Referring initially to FIG. 1, an orthopedic knee brace, generally designated 10, is shown operatively mounted on the leg 11 of a person requiring or desiring added external support and/or stabilization of the knee joint 12. When worn on the leg 11, the orthopedic knee brace 10 specifically engages the knee joint 12, the upper leg 13 above the knee joint 12 and the lower leg 14 below the knee joint 12.

There are a number of relative terms defined below which are used in the following description to distinguish various elements of the orthopedic knee brace 10 from one another, but which are not to be construed as limiting the scope of the invention. The relative terms "medial" and "lateral" characterize certain elements of the orthopedic knee brace 10 and, in particular, describe the relative proximity of the given element to the central longitudinal axis of the body of a wearer when the brace 10 is mounted thereon. A "medial" element is closer to the central longitudinal axis of the body, while a "lateral" element is further from the central longitudinal axis of the body. The terms "upper" and "lower" describe the position of certain elements of the brace 10 as being either above or below a horizontal plane running through the central rotational joint of the brace 10. In particular, an "upper" element is above the horizontal plane running through the central rotational joint of the brace 10, while a "lower" element is below the horizontal plane running through the central rotational joint of the brace 10. The relative terms "posterior" and "anterior" characterize certain elements of the orthopedic knee brace 10 and, in particular, describe the orientation of the given element relative to the body of the wearer when the brace 10 is mounted thereon. A "posterior" element faces the body of the wearer, while an "anterior" element faces the exterior of the brace 10 away from the body of the wearer.

The orthopedic knee brace 10 comprises a frame 16 which includes an upper support member 18, a lower support member 20, a lateral hinge assembly 22, and a medial hinge assembly 24. The orthopedic knee brace 10 also includes a plurality of straps 26 and strap retainers 28 for maintaining the position of the orthopedic knee brace 10 on the leg 11 of the wearer. The general features of the frame 16, straps 26 and strap retainers 28, but not the specific features of the present invention, are disclosed in commonly-owned U.S. Pat. Nos. 7,485,103 and/or 7,479,122, both of which are incorporated herein by reference.

Figure 2:
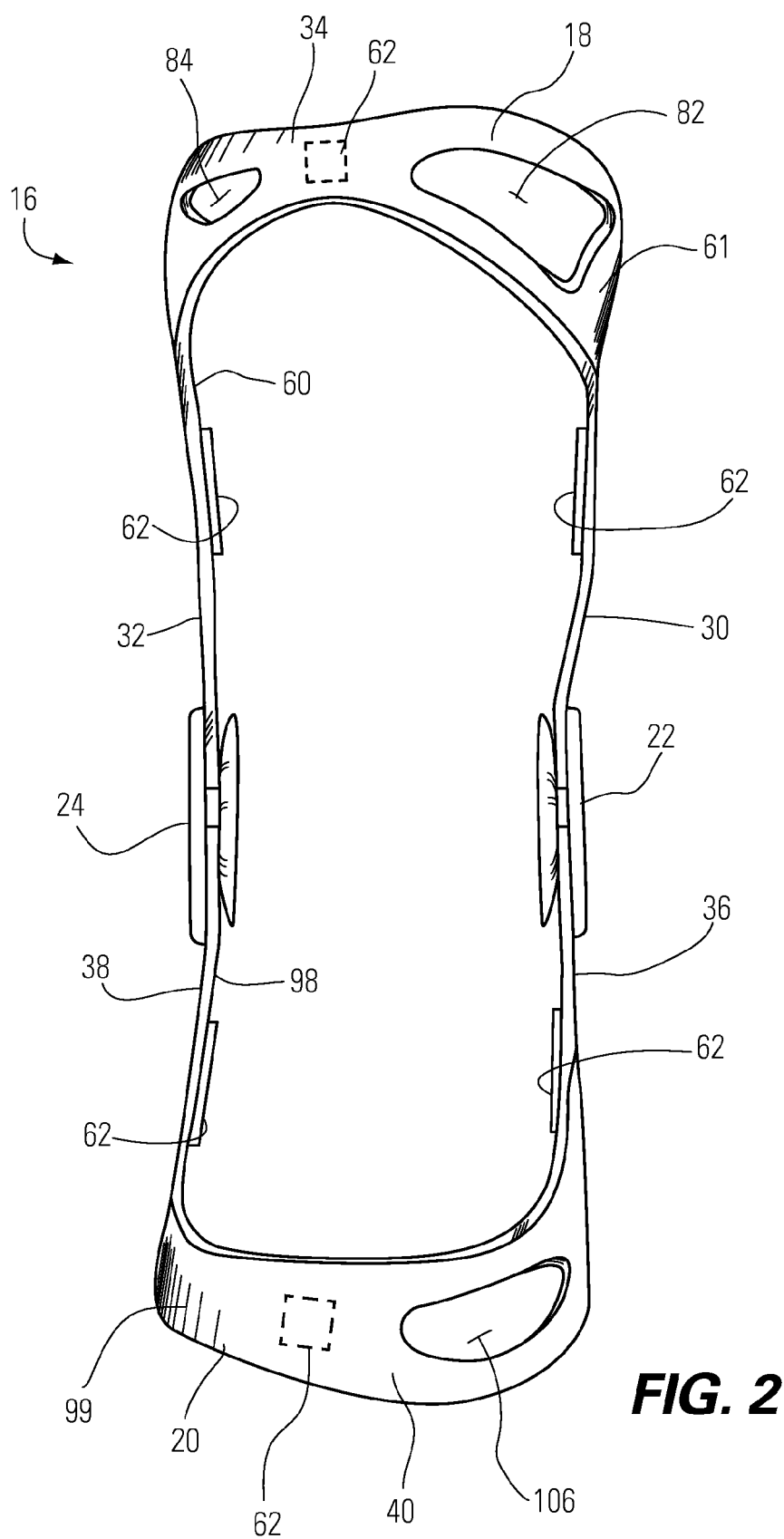
FIG. 2 is a frontal view of the frame included within the orthopedic brace of FIG. 1.

Referring additionally to FIG. 2 wherein only the frame 16 is shown, the upper support member 18 is a unitary construction comprising a lateral upper arm 30, a medial upper arm 32, and an arcuate upper cuff 34 connectively extending between the lateral and medial upper arms 30, 32. The lower support member 20 is likewise a unitary construction comprising a lateral lower arm 36, a medial lower arm 38, and an arcuate lower cuff 40 connectively extending between the lateral and medial lower arms 36, 38. Although not shown, either upper arm 30, 32 or lower arm 36, 38 may include one or more integral offset hinges as described in U.S. Pat. Nos. 7,485,103 and 7,479,122 to provide the frame with unbalanced medio-lateral flexibility characteristics. Alternatively, the one or more integral offset hinges may be omitted from the upper arms 30, 32 or lower arms 36, 38 as shown in FIG. 1 so that the frame 16 has essentially balanced medio-lateral flexibility characteristics. The lateral and medial hinge assemblies 22, 24 may be of a generalized conventional construction, such as described in U.S. Pat. No. 7,479,122, or either lateral or medial hinge assembly 22, 24 may be of a specific type of construction, such as described in U.S. Pat. No. 7,485,103.

When the orthopedic knee brace 10 is mounted on the leg 11 of the wearer as shown in FIG. 1, the lateral upper arm 30 is substantially vertically oriented and adjacent to the lateral side of the upper leg 13, the medial upper arm 32 is substantially vertically oriented and adjacent to the medial side of the upper leg 13, and the upper cuff 34 is substantially horizontally oriented, extending across the front of the upper leg 13, which is commonly termed the thigh. Similarly, the lateral lower arm 36 is substantially vertically oriented and adjacent to the lateral side of the lower leg 14, the medial lower arm 38 is substantially vertically oriented and adjacent to the medial side of the lower leg 14, and the lower cuff 40 is substantially horizontally oriented, extending across the front of the lower leg 14, which is commonly termed the shin. The lateral hinge assembly 22 is positioned adjacent to the lateral knee condyle and the medial hinge assembly 24 is positioned adjacent to the medial knee condyle.

The orthopedic knee brace 10 further comprises a plurality of pads including an upper pad 42, a lower pad 44, a lateral condyle pad 46 and a medial condyle pad 48. The lateral and medial condyle pads 46, 48 are adapted to the configuration of the lateral and medial hinge assemblies 22, 24, respectively. The anterior faces of the lateral and medial condyle pads 46, 48 are releasably fastened to the posterior faces of the lateral and medial hinge assemblies 22, 24, respectively, by releasable fastening means (not shown) such as hook and loop fasteners commonly known by the trade name VELCRO. As such, the lateral and medial condyle pads 46, 48 are positioned between the posterior faces of the lateral and medial hinge assemblies 22, 24 and the lateral and medial condyles of the knee joint 14, respectively, when the orthopedic knee brace 10 is mounted on the leg 11 of the wearer to cushion the knee joint 14 from the rigid structure of the hinge assemblies 22, 24.

Figure 3:
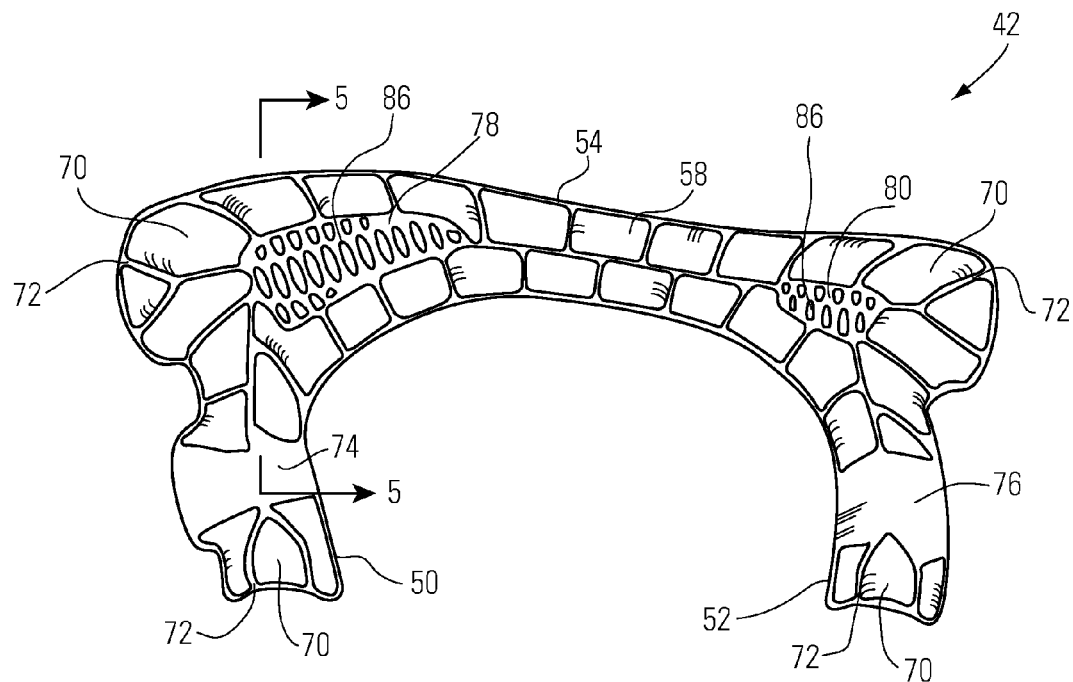
FIG. 3 is a posterior view of an upper pad included within the orthopedic brace of FIG. 1.
Figure 4:
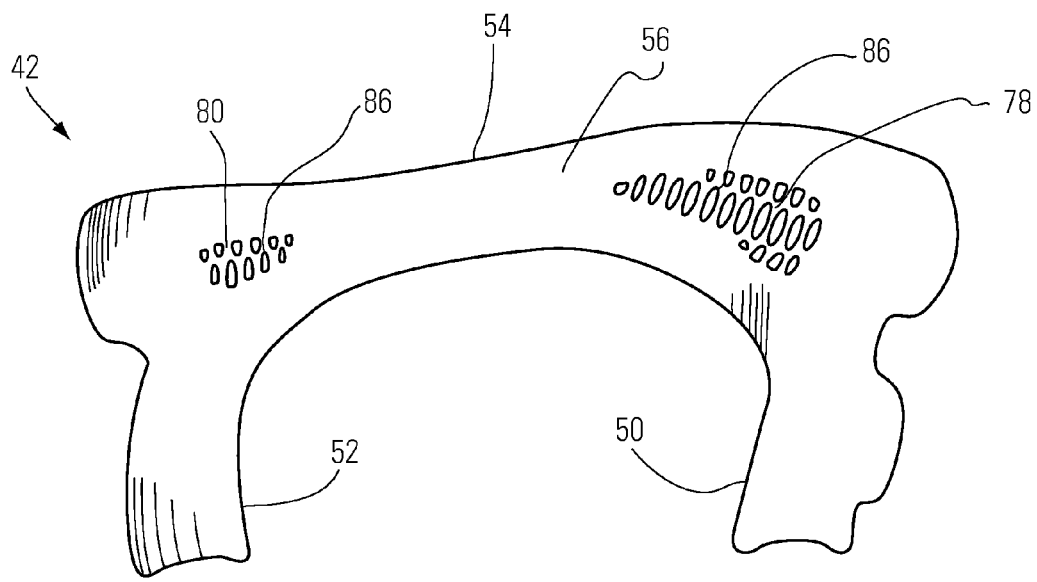
FIG. 4 is an anterior view of the upper pad of FIG. 3.

Referring additionally to FIGS. 3 and 4, the upper pad 42 is adapted to the configuration of the upper support member 18. Accordingly, the upper pad 42 is characterized by a lateral upper arm portion 50, a medial upper arm portion 52 and an upper cuff portion 54. The lateral upper arm portion 50 has an outline corresponding to the lateral upper arm 30 of the upper support member 18 and is flexed from its planar construction shown in FIGS. 3 and 4 into cooperative engagement with the curved contours of the lateral upper arm 30 as shown in FIG. 1. The medial upper arm portion 52 has an outline corresponding to the medial upper arm 32 of the upper support member 18 and is flexed from its planar construction into cooperative engagement with the curved contours of the medial upper arm 32. The upper cuff portion 54 has an outline corresponding to the upper cuff 34 of the upper support member 18 and is flexed from its planar construction into cooperative engagement with the curved contours of the upper cuff 34.

The upper pad 42 has an anterior face 56 and a posterior face 58. The anterior face 56 of the upper pad 42 is relatively even and smooth. The anterior face 56 of the upper pad 42 engages and is releasably fastened to a posterior face 60 (i.e., inside face) of the upper support member 18, which is likewise relatively even and smooth, by releasable fastening means, preferably hook and loop fasteners (VELCRO). The upper support member 18 also has a relatively even and smooth anterior face 61 (i.e., outside face).

In a preferred embodiment, the anterior face 56 of the upper pad 42 integrally formed from a fabric which is the loop material of the hook and loop fastener. A plurality of patches of the hook material 62 are affixed to the posterior face 60 of the upper support member 18 at spaced apart intervals (shown in FIG. 2) by substantially any permanent fastening means such as glue or the like. In any case, the upper pad 42 is positioned between the upper support member 18 and the upper leg 13 with the anterior face 56 of the upper pad 42 engaging the posterior face 60 of the upper support member 18 and the posterior face 58 of the upper pad 42 engaging the upper leg 13 when the orthopedic knee brace 10 is mounted on the leg 11 which effectively cushions the upper leg 13 from the rigid structure of the upper support member 18.

The term "rigid" as used herein generally encompasses structures which are deemed either rigid or semi-rigid as these terms are commonly understood. The upper support member 18 is characterized as "rigid" to the extent it is substantially less flexible, i.e., substantially stiffer, than the upper pad 42 which is characterized as non-rigid. Exemplary rigid materials of construction for the upper support member 18 include metals, plastics, fiberglass, laminates, combinations thereof, or other similar relatively stiff materials. Exemplary non-rigid materials of construction for the upper pad 42 include foams, textiles and other fabrics, combinations thereof, or other similar relatively pliant materials. Details of a preferred construction for the upper pad 42 are set forth below.

Figure 5:
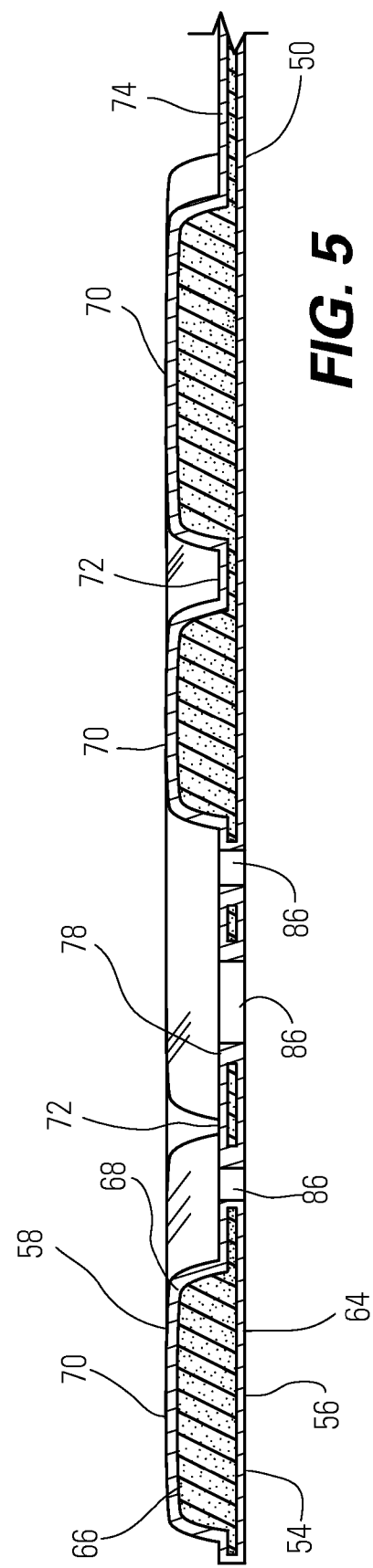
FIG. 5 is partial cross-sectional view of the upper pad of FIG. 3, which is taken along line 5-5 in FIG. 3.

Referring to FIGS. 3-5, the upper pad 42 has an integrated laminate construction comprising in series three essentially planar layers, namely an anterior external layer 64, an internal layer 66 and a posterior external layer 68. The anterior and posterior external layers 64, 68 are continuously and permanently bonded to the internal layer 66 along substantially the entirety of the anterior and posterior faces of the internal layer 66, respectively, to create an essentially planar unitary pad structure. As such the anterior external layer 64 forms the anterior face 56 of the upper pad 42 and the posterior external layer 68 forms the posterior face 58 of the upper pad 42. Bonding is effected by substantially any conventional bonding means such as gluing, thermal welding, ultrasonic welding, or the like.

As noted above, the upper pad 42 is characterized as non-rigid or relatively less rigid and more flexible than the upper support member 18 of the orthopedic knee brace 10. The flexibility of the upper pad 42 is attributable in part to the relatively pliable, i.e., flexible, materials from which the upper pad 42 is fabricated. In particular, the anterior and posterior external layers 64, 68 are preferably fabricated from a cloth material such as a plush or a pile which is capable of functioning as a loop material for a hook and loop fastener. The internal layer 66 is preferably fabricated from an elastically compressible material, such as an open-cell or closed-cell foam or other sponge-like material.

The flexibility of the upper pad 42 is also attributable in part to its surface configuration. The upper pad 42 is aptly described above as being an essentially planar structure. However, the posterior face 58 of the upper pad 42 is more specifically characterized as being contoured by a plurality of raised regions 70 distributed across the posterior face 58 which appear as flat-topped mesa-like structures. The raised regions 70 are separated from one another by a plurality of interstitial flexion channels 72 which appear as a network of steep narrow flat-bottomed valleys running between the raised regions 70 to define the perimeter shape of each raised region 70. The flexion channels 72 are characterized as being substantially thinner (i.e., less thick) than the raised regions 70. Stated alternatively, the raised regions 70 are characterized as being substantially thicker (i.e., less thin) than the flexion channels 72. The combination of raised regions 70 and flexion channels 72 produces an uneven irregular quilt-like pattern on the posterior face 58 of the upper pad 42 while the opposite anterior face 56 of the upper pad 42 remains comparatively smooth.

The thinner flexion channels 72 provide lines along which the upper pad 42 is even more flexible than the raised regions 70 of the upper pad 42. As such, the flexion channels 72 more readily enable one to adapt, i.e., conform, the upper pad 42 to the curved and/or irregular surface contours of the less flexible upper leg 13 of the wearer which the upper pad 42 posteriorly engages. The flexion channels 72 also more readily enable one to adapt the upper pad 42 to the curved and/or irregular surface contours of the likewise less flexible upper support member 18 which the upper pad 42 anteriorly engages.

The enhanced adaptability of the upper pad 42 to the abutting contoured surfaces of the upper leg 13 and the upper support member 18 correspondingly enhances the fit of the orthopedic knee brace 10 to the leg 11 of the wearer. A desirable result of this enhanced fit is that the brace 10 resists slippage and displacement from its preferred position on the leg 11 during normal activity by the wearer, thereby improving the suspension of the brace 10 on the leg 11 of the wearer. Among the advantageous effects that the adapted upper pad 42 imparts generally to the orthopedic knee brace 10 are increased comfort to the wearer of the brace 10 and improved functional performance of the brace 10 for its intended purpose of supporting and/or stabilizing the knee joint 14.

The network of flexion channels 72 also provides ventilation pathways between the ambient external environment surrounding the wearer of the orthopedic knee brace 10 and the skin on the upper leg 13 of the wearer which engages the upper pad 42. In particular, the flexion channels 72 facilitate the flow of fresh air onto the skin of the upper leg 13 behind the upper pad 42, effectively cooling the skin and reducing the likelihood of perspiration build-up between the skin and the upper pad 42 which could cause discomfort to the wearer of the brace 10 and cause undesirable slippage and displacement of the brace 10 on the leg 11.

The posterior face 58 of the upper pad 42 is additionally contoured by a pair of upper strap clearance segments. A lateral upper strap clearance segment 74 is formed in the posterior face 58 of the upper pad 42 on the lateral upper arm portion 50. A medial upper strap clearance segment 76 is similarly formed in the posterior face 58 of the upper pad 42, but on the medial upper arm portion 52. The lateral and medial upper strap clearance segments 74, 76 are characterized as being substantially thinner than the raised regions 70 and having a thickness comparable to the flexion channels 72. The position of the upper strap clearance segments 74, 76 corresponds to the position of the particular strap 26a circling behind the upper leg 13 proximal to the medial and lateral hinge assemblies 20, 22 when the orthopedic knee brace 10 is mounted on the leg 11 as shown in FIG. 1. The reduced profile of the upper strap clearance segments 74, 76 enables them to receive the strap 26a therein between the adjoining raised regions 70 bounding the upper strap clearance segments 74, 76 on either side and act as a strap guide to minimize interference by the upper pad 42 with the function of the strap 26a.

Referring back to FIGS. 1 and 2 as well as FIGS. 3-5, additional ventilation of the skin on the upper leg 13 behind the upper pad 42 is provided by a pair of mesh sections included in the upper pad 42, namely, a lateral upper mesh section 78 and a medial upper mesh section 80, and a pair of cooperatively corresponding upper ventilation windows included in the upper support member 18, namely, a lateral upper ventilation window 82 and a medial upper ventilation window 84. The lateral and medial upper mesh sections 78, 80 are integral with the overall construction of the upper pad 42 and both have essentially the same characteristics as one another. In particular, each upper mesh section 78, 80 is characterized as an area of the upper pad 42 integrally formed from the above-described laminate which is highly flexible, is substantially thinner than the raised regions 70 and has a thickness comparable to the flexion channels 72.

Each upper mesh section 78, 80 has a plurality of small void spaces 86 formed therein which are interspersed across the entire surface of the laminate and which extend entirely through the entire thickness of the laminate. Accordingly, a substantial fraction of the surface area of each upper mesh section 78, 80 is void or open and, more preferably, at least the majority of the surface area of each upper mesh section 78, 80 is void or open.

Each upper ventilation window 82, 84 of the upper support member 18 similarly extends entirely through the entire thickness of the upper support member 18 overlying the upper pad 42. However, in contrast to the upper mesh sections 78, 80, each upper ventilation window 82, 84 is an expansive opening which is a complete void and entirely devoid of any obstructions or any other limiting structures. The remainder of the surface of the upper support member 18 apart from the ventilation windows 82, 84 is an essentially continuous uninterrupted surface lacking openings and, as such, does not freely allow air to pass therethrough.

The lateral upper mesh section 78 is positioned on the lateral side of the upper cuff portion 54 of the upper pad 42 so that it aligns with the lateral upper ventilation window 82, which is correspondingly positioned on the lateral side of the upper cuff 34 of the upper support member 18. The medial upper mesh section 80 is opposingly positioned on the medial side of the upper cuff portion 54 of the upper pad 42 so that it aligns with the medial upper ventilation window 84, which is correspondingly positioned on the medial side of the upper cuff 34 of the upper support member 18. Accordingly, the lateral upper mesh section 78, in cooperation with the lateral upper ventilation window 82, exposes the skin on the upper leg 13 behind the lateral side of the upper cuff 34 to the ambient external environment when the orthopedic knee brace 10 is mounted on the leg 11. The medial upper mesh section 80, in cooperation with the medial upper ventilation window 84, similarly exposes the skin on the upper leg 13 behind the medial side of the upper cuff 34 to the ambient external environment. The net effect of this construction is to further facilitate the flow of fresh air onto the skin of the upper leg 13 behind the upper support member 18 and intervening upper pad 42.

Although the lateral and medial upper mesh sections 78, 80 are constructed to permit the free flow of air therethrough, the mesh construction also advantageously inhibits the undesirable effects of edema in the part of the body behind the lateral and medial upper ventilation windows 82, 84 by impeding the expansive swelling of body tissue out the upper ventilation windows 82, 84 of the upper support member 18. In particular, the void spaces 86 are sized sufficiently large to freely permit air flow through the mesh sections 78, 80 of the upper pad 42, but are sized sufficiently small to inhibit the extrusion of skin on the leg 11 through the mesh sections 78, 80. The remainder of the surface of the upper pad 42 apart from the mesh sections 78, 80 is an essentially continuous uninterrupted surface lacking openings and, as such, does not freely allow air to pass therethrough.

The present invention is not limited to any one particular method for fabricating the upper pad 42. Nevertheless, a preferred method for fabricating the upper pad 42 comprises selecting a first sheet of a first flexible material, a second sheet of a second flexible material, and a third sheet of a third flexible material. The first, second, and third sheets preferably all have substantially uniform thicknesses wherein the uniform thickness of the second sheet is preferably substantially greater than the uniform thicknesses of the first and third sheets which are preferably equal. The first and third materials are preferably a cloth material and are preferably the same material. The third material is preferably different from the first and third materials and is preferably an elastically compressible foam material. The first and third materials will ultimately make up the anterior and posterior external layers 64, 68 of the upper pad 42, respectively, and the second material will ultimately make up the internal layer 66 of the upper pad 42 in a manner described below.

A laminate of essentially uniform thickness is formed by stacking the first, second and third sheets one atop the other such that the second sheet is sandwiched between the first and third sheets with the interior surface of the first sheet continuously engaging one surface of the second sheet and the interior surface of the third sheet continuously engaging the opposite surface of the second sheet. The three sheets are essentially permanently and continuously bonded together across substantially the entirety of their engaged surfaces in a manner described above to create the laminate. A blank is cut out of the laminate based on a pattern matching an outline of the upper pad 42.

The raised regions 70, flexion channels 72, upper strap clearance segments 74, 76, and upper mesh sections 78, 80 for the upper pad 42 are formed in the blank by compressing (and optionally thermally or ultrasonically energizing) the blank from the direction of its posterior surface. In particular, a compression force (and optional thermal or ultrasonic energy) is directed against the posterior surface at the precise desired locations of the flexion channels 72, upper strap clearance segments 74, 76, and upper mesh sections 78, 80, respectively, which exceeds the elasticity limit of the second material. As such, the contours of these structures are permanently impressed into the second and third materials of the blank. Formation of the upper mesh sections 78, 80 is completed by additionally cutting out the void spaces 86 from the laminate at their precise desired locations using a punch or the like. The perimeter of the blank may also be trimmed further to more precisely match the desired pad outline, thereby completing fabrication of the upper pad 42.

It is alternately within the scope of the present invention to modify the above-described fabrication by switching the sequence of the stacking step, the bonding step and/or the cutting step, so that the sheets are cut to the outline of the upper pad 42 before the sheets are stacked and/or bonded. In any case, it is noted that the resulting upper pad 42 typically maintains a planar configuration as shown in FIGS. 3 and 4 until manually flexed into a contoured configuration for engagement with the upper support member 18. If the upper pad 42 is subsequently disengaged from the upper support member 18, it is readily returned to its planar configuration.

Figure 6:
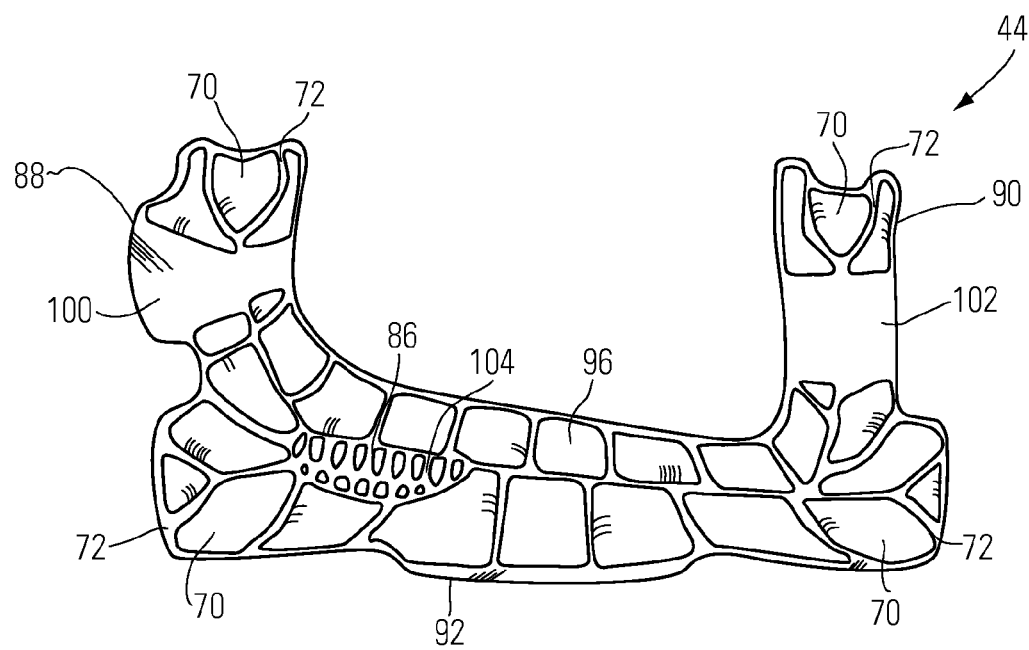
FIG. 6 is a posterior view of a lower pad included within the orthopedic brace of FIG. 1.
Figure 7:
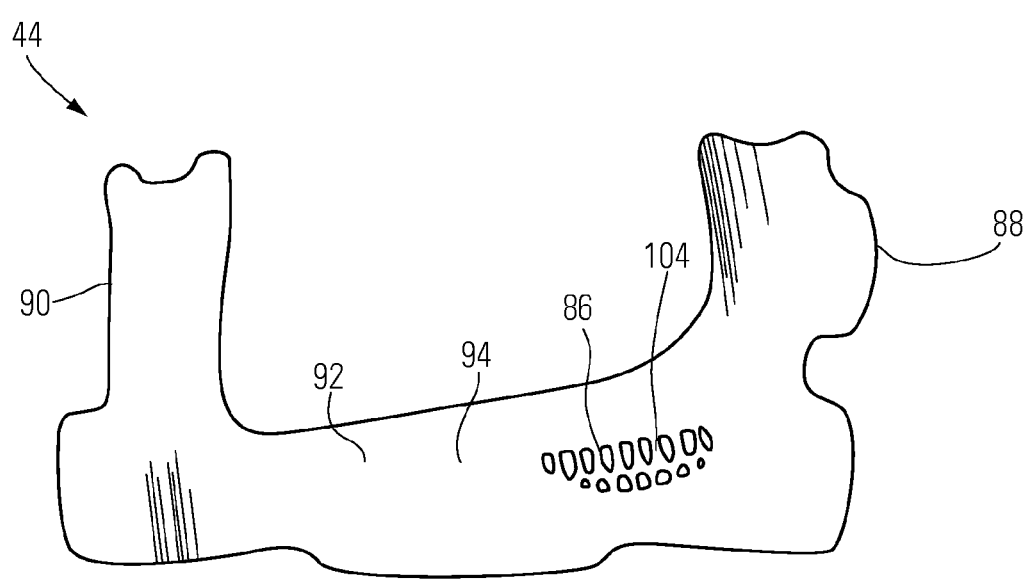
FIG. 7 is an anterior view of the lower pad of FIG. 6.

The above-recited description of the configuration, properties and method of fabrication for the upper pad 42 applies essentially the same to the lower pad 44. In particular, with added reference to FIGS. 6 and 7, the lower pad 44 is adapted to the configuration of the lower support member 20. As such, the lower pad 44 has a lateral lower arm portion 88, a medial lower arm portion 90 and a lower cuff portion 92. The lateral lower arm portion 88 has an outline corresponding to the lateral lower arm 36 of the lower support member 20 and is flexed from its planar construction shown in FIGS. 6 and 7 into cooperative engagement with the curved contours of the lateral lower arm 36 as shown in FIG. 1. The medial lower arm portion 90 has an outline corresponding to the medial lower arm 38 of the lower support member 20 and is flexed from its planar construction into cooperative engagement with the curved contours of the medial lower arm 38. The lower cuff portion 92 has an outline corresponding to the lower cuff 40 of the lower support member 20 and is flexed from its planar construction into cooperative engagement with the curved contours of the lower cuff 40.

The lower pad 44 has an anterior face 94 and a posterior face 96. The anterior face 94 of the lower pad 44 is relatively even and smooth. The anterior face 94 of the lower pad 44 engages and is releasably fastened to a posterior face 98 (i.e., inside face) of the lower support member 20, which is likewise relatively even and smooth, by releasable fastening means as described above with respect to the upper pad 42. The lower support member 20 also has a relatively even and smooth anterior face 99 (i.e., outside face). The lower pad 44 has the same integrated laminate construction as the upper pad 42 and the posterior face 96 of the lower pad 44 is likewise contoured by raised regions 70 and flexion channels 72 to provide the lower pad 44 with the same advantageous flexion and ventilation characteristics as the upper pad 42.

The posterior face 96 of the lower pad 44 is also contoured by a pair of lower strap clearance segments which are essentially the same as the upper strap clearance segments 74, 76 of the upper pad 42. A lateral lower strap clearance segment 100 is formed in the posterior face 96 on the lateral lower arm portion 88 of the lower pad 44. A medial lower strap clearance segment 102 is similarly formed in the posterior face 96, but on the medial lower arm portion 90 of the lower pad 44. The position of the lateral and medial lower strap clearance segments 100, 102 corresponds to the position of the particular strap 26b circling behind the lower leg 14 proximal to the medial and lateral hinge assemblies 20, 22 when the orthopedic knee brace 10 is mounted on the leg 11 as shown in FIG. 1. The reduced profile of the lower strap clearance segments 100, 102 minimizes interference by the lower pad 44 with the function of the strap 26b.

Additional ventilation of the skin on the lower leg 14 behind the lower pad 44 is provided by a single lower mesh section 104 in the lower pad 44 and a cooperatively corresponding lower ventilation window 106 in the lower support member 20. The lower mesh section 104 and a lower ventilation window 106 have essentially the same configuration and function as the upper mesh sections 78, 80 and the upper ventilation windows 82, 84 in the upper pad 42 and upper support member 18. In particular, the lower mesh section 104 is integral with the overall construction of the lower pad 44. The lower mesh section 104 has void spaces 86 and is positioned on the lateral side of the lower cuff portion 92 of the lower pad 44 so that it aligns with the lower ventilation window 106 which is correspondingly positioned on the lateral side of the lower cuff 40 of the lower support member 20. Accordingly, the lower mesh section 104, in cooperation with the lower ventilation window 106, exposes the skin on the lower leg 14 behind the lateral side of the lower cuff 40 to the ambient external environment when the orthopedic knee brace 10 is mounted on the leg 11. This further facilitates the flow of fresh air onto the skin of the lower leg 14 behind the lower support member 20 and intervening lower pad 44 while advantageously inhibiting the effects of edema in the part of the body behind the lower ventilation window 106.

The present invention has been described in the context of a specific exemplary orthopedic knee brace 10 solely for purposes of illustration. It is understood by one of ordinary skill in the art that the present invention is generally applicable to any number of other orthopedic knee braces and is even more broadly applicable to any orthopedic brace for the body having at least one support member and pad constructed in accordance with the instant teaching.

While the forgoing preferred embodiments of the invention have been described and shown, it is understood that alternatives and modifications, such as those suggested and others, may be made thereto and fall within the scope of the invention.

We claim:

1. An orthopedic brace comprising:
a pliable pad fabricated from a laminate, said pliable pad having a first face and a second face and areally segmented into a first portion and a second portion, wherein said first portion of said pliable pad lacks any void spaces extending entirely through said first portion of said pliable pad from said first face to said second face of said pliable pad, thereby preventing free air flow through said first portion of said pliable pad from said first face to said second face of said pliable pad, and wherein said second portion of said pliable pad consists essentially of one or more mesh sections integrally formed in said laminate, each of said one or more mesh sections having a plurality of void spaces extending entirely through said second portion of said pliable pad from said first face to said second face of said pliable pad, thereby freely permitting air flow through said second portion of said pliable pad from said first face to said second face of said pliable pad; and
a rigid support member having a first face and a second face and areally segmented into a first portion and a second portion, wherein said second portion of said rigid support member consists essentially of one or more open ventilation windows, each of said one or more open ventilation windows extending entirely through said second portion of said rigid support member from said first face to said second face of said rigid support member, thereby freely permitting air flow through said second portion of said rigid support member from said first face to said second face of said rigid support member, and wherein said first portion of said rigid support member lacks any ventilation windows extending entirely through said first portion of said rigid support member from said first face to said second face of said rigid support member, thereby preventing free air flow through said first portion of said rigid support member from said first face to said second face of said rigid support member, and further wherein said rigid support member overlays said pliable pad such that said second portion of said rigid support member is aligned with essentially the entirety of said second portion of said pliable pad to freely permit air flow through said second portion of said rigid support member and said second portion of said pliable pad in series and such that said first portion of said rigid support member is aligned with essentially the entirety of said first portion of said pliable pad to prevent free air flow through said first portion of said rigid support member and said first portion of said pliable pad in series.

2. The orthopedic brace of claim 1 wherein said laminate has a unitary construction comprising a first layer formed from a first material and a second layer formed from a second material.

3. The orthopedic brace of claim 2 wherein said laminate further comprises a third layer and said second layer is positioned between said first layer and said third layer.

4. The orthopedic brace of claim 3 wherein said third layer is formed from said first material.

5. The orthopedic brace of claim 2 wherein said first material is a flexible fabric.

6. The orthopedic brace of claim 2 wherein said second material is an elastically compressible foam.

7. The orthopedic brace of claim 1 wherein said first portion of said pliable pad includes a raised region, wherein said second portion of said pliable pad is substantially thinner than said raised region.

8. The orthopedic brace of claim 7 wherein said raised region is a first raised region, said pliable pad having a second raised region and a flexion channel between said first and second raised regions, and wherein said flexion channel is substantially thinner and more flexible than said first or second raised region enabling said pliable pad to more freely flex along said flexion channel than across said first or second raised region.

9. The orthopedic brace of claim 8 further comprising a strap connectable to said rigid support member, wherein said pliable pad has a third raised region and a strap clearance segment substantially thinner than said first, second or third raised region, and wherein said strap clearance segment is positioned between said second and third raised regions and receives said strap when said strap is connected to said rigid support member.

10. The orthopedic brace of claim 1 wherein each void space of said plurality of void spaces is sufficiently large to freely permit air flow through said second portion of said pliable pad from said first face to said second face of said pliable pad, but each void space of said plurality of void spaces is sufficiently small to inhibit extrusion of skin on a body of a wearer through said second portion of said pliable pad from said first face to said second face of said pliable pad.

11. The orthopedic brace of claim 1 wherein said orthopedic brace is an orthopedic knee brace and said rigid support member is configured to engage an upper leg of a brace wearer or a lower leg of the brace wearer.

12. An orthopedic brace comprising:
a pliable pad having a posterior face and an anterior face and fabricated from a laminate having an anterior external layer formed from a first flexible material, an internal layer formed from an elastically compressible material, and a posterior external layer formed from a second flexible material, said pliable pad areally segmented into a first portion and a second portion, wherein said first portion of said pliable pad includes a first raised region, a second raised region separated by a flexion channel substantially thinner than said first or second raised region enabling said pliable pad to more freely flex along said flexion channel than across said first or second raised region and wherein said first portion of said pliable pad lacks any void spaces extending entirely through said first portion of said pliable pad from said posterior face to said anterior face of said pliable pad, thereby preventing free air flow through said first portion of said pliable pad from said posterior face to said anterior face of said pliable pad, and wherein said second portion of said pliable pad consists essentially of one or more mesh sections integrally formed in said laminate and substantially thinner than said first raised region or said second raised region, each of said one or more mesh sections having a plurality of void spaces extending entirely through said section portion of said pliable pad from said posterior face to said anterior face of said pliable pad, thereby freely permitting air flow through said second portion of said pliable pad from said posterior face to said anterior face of said pliable pad; and a rigid support member having an anterior face and a posterior face and areally segmented into a first portion and a second portion, wherein said second portion of said rigid support member consists essentially of one or more open ventilation windows, each of said one or more open ventilation windows extending entirely through said second portion of said rigid support member from said posterior face to said anterior face of said rigid support member, thereby freely permitting air flow through said second portion of said rigid support member from said posterior face to said anterior face of said rigid support member, and wherein said first portion of said rigid support member lacks any ventilation windows extending entirely through said first portion of said rigid support member from said posterior face to said anterior face of said rigid support member, thereby preventing free air flow through said first portion of said rigid support member from said posterior face to said anterior face of said rigid support member, and further wherein said rigid support member overlays said pliable pad such that said anterior face of said pliable pad engages said posterior face of said rigid support member and said second portion of said rigid support member is aligned with essentially the entirety of said second portion of said pliable pad to freely permit air flow through said second portion of said rigid support member and said second portion of said pliable pad in series and such that said first portion of said rigid support member is aligned with essentially the entirety of said first portion of said pliable pad to prevent free air flow through said first portion of said rigid support member and said first portion of said pliable pad in series.

13. The orthopedic brace of claim 12 wherein said first flexible material and said second flexible material of said laminate are identical material.

14. The orthopedic brace of claim 13 wherein said first and second flexible material are a fabric.

15. The orthopedic brace of claim 12 wherein each void space of said plurality of void spaces is sufficiently large to freely permit air flow through said second portion of said pliable pad from said posterior face to said anterior face of said pliable pad, but each void space of said plurality of void spaces is sufficiently small to inhibit extrusion of skin on a body of a wearer through said second portion of said pliable pad from said posterior face to said anterior face of said pliable pad.

16. The orthopedic brace of claim 12 wherein said second portion of said pliable pad is substantially thinner than said first raised region or said second raised region as a result of said internal layer of said elastically compressible material in said laminate being substantially thinner in said second portion of said pliable pad than in said first raised region or said second raised region.

17. An orthopedic brace comprising:
a pliable pad fabricated from a laminate including a layer of an elastically compressible foam, said pliable pad having a first face and a second face and areally segmented into a first portion and a second portion, wherein said first portion of said pliable pad includes a raised region having a first pad thickness and said first portion of said pliable pad lacks any void spaces extending entirely through said first portion of said pliable pad from said first face to said second face of said pliable pad, thereby preventing free air flow through said first portion of said pliable pad from said first face to said second face of said pliable pad, and wherein said second portion of said pliable pad consists essentially of one or more mesh sections integrally formed in said laminate and having a second pad thickness substantially less than said first pad thickness, each of said one or more mesh sections having a plurality of void spaces extending entirely through said second portion of said pliable pad from said first face to said second face of said pliable pad, thereby freely permitting air flow through said second portion of said pliable pad from said first face to said second face of said pliable pad; and a rigid support member having a first face and a second face and areally segmented into a first portion and a second portion, wherein said second portion of said rigid support member consists essentially of one or more open ventilation windows, each of said one or more open ventilation windows extending entirely through said second portion of said rigid support member from said first face to said second face of said rigid support member, thereby freely permitting air flow through said second portion of said rigid support member from said first face to said second face of said rigid support member, and wherein said first portion of said rigid support member lacks any ventilation windows extending entirely through said first portion of said rigid support member from said first face to said second face of said rigid support member, thereby preventing free air flow through said first portion of said rigid support member from said first face to said second face of said rigid support member, and further wherein said rigid support member overlays said pliable pad such that said second portion of said rigid support member is aligned with essentially the entirety of said second portion of said pliable pad to freely permit air flow through said second portion of said support rigid member and said second portion of said pliable pad in series and such that said first portion of said rigid support member is aligned with essentially the entirety of said first portion of said pliable pad to prevent free air flow through said first portion of said rigid support member and said first portion of said pliable pad in series.

18. The orthopedic brace of claim 17 wherein said second pad thickness is substantially less than said first pad thickness as a result of said layer of said elastically compressible foam in said laminate being substantially thinner in said second portion of said pliable pad than in said first portion of said pliable pad.

* * * * *